(12) United States Patent
Okino et al.

(10) Patent No.: US 8,258,178 B2
(45) Date of Patent: Sep. 4, 2012

(54) **AGENTS FOR PREVENTING ATTACHMENT OF BARNACLE CONSISTING OF ORGANIC SOLVENT EXTRACTS OF RED ALGA *LAURENCIA* SP. AND COMPOUNDS ISOLATED THEREFROM**

(75) Inventors: Tatsufumi Okino, Hokkaido (JP); Yasuyuki Nogata, Chiba (JP)

(73) Assignee: Central Research Institute of Electric Power Industry, Tokyo (JP)

( * ) Notice: Subject to any disclaimer, the term of this patent is extended or adjusted under 35 U.S.C. 154(b) by 282 days.

(21) Appl. No.: 12/733,489

(22) PCT Filed: Sep. 5, 2008

(86) PCT No.: PCT/JP2008/066040
§ 371 (c)(1),
(2), (4) Date: Apr. 12, 2010

(87) PCT Pub. No.: WO2009/031637
PCT Pub. Date: Mar. 12, 2009

(65) Prior Publication Data
US 2010/0204315 A1    Aug. 12, 2010

(30) Foreign Application Priority Data
Sep. 7, 2007   (JP) .................................. 2007-232589

(51) Int. Cl.
*A61K 31/343* (2006.01)
*C07D 307/77* (2006.01)
(52) U.S. Cl. ...................................... 514/468; 549/458
(58) Field of Classification Search .................. 514/468; 549/458
See application file for complete search history.

(56) References Cited

FOREIGN PATENT DOCUMENTS
JP    2007-045811 A    2/2007
WO    WO 99/01514      1/1999

OTHER PUBLICATIONS

Tsuyoshi Abe et al., "Chemical Races in the Red Alga *Laurencia nipponica* (Rhodomelaceae, Ceramiales)", *Phycological Research*, vol. 47, Issue 2, pp. 87-95 (1999).
Minoru Suzuki et al., "Halogenated secondary metabolites from Japanese species of the red algal genus *Laurencia* (Rhodomelaceae Ceramiales)", *Current Topics in Phytochemistry*, Jan. 1, 2005, pp. 1-34.
European Office Action dated Oct. 19, 2011 for EP 08 829 481.4.
Partial European Search Report dated Oct. 27, 2011 for EP 11 18 3268.
R. Dy Nys et al, "The need for standardized broad scale bioassay testing. A case study using the red alga *Laurencia rigida*", *Biofouling*, 10(1-3) pp. 213-224 (1996).
B.A.P. Da Gama et al, "The effects of seaweed secondary metabolites on biofouling", *Biofouling*, 18(1), pp. 13-20 (2002).
G. Ryu et al, Studies on marine natural antifoulant laurinterol, *Han'guk Hwaniyong Uisaeng Hakhoechi*, (*Korean J. Of Environmental Health*), 29(3) pp. 1-8 (2003).
Supplementary European Search Report mailed Mar. 10, 2011 in EP 08 829 481.
Geonseek Ryu et al., "Studies on Marine Natural Antifoulant Laurinterol," Chemical Abstract Service, Columbus, Ohio, database accession No. 2004:491698, Abstract XP-002622083.
Matsuo Y; Suzuki M; Masuda M, "Enshuol, a Novel Squalene-derived Pentacyclic Triterpene Alcohol from a New Species of the Red Algal Genus *Laurencia*," *Chemistry Letters*, vol. 24, 1995, pp. 1043-1044.

*Primary Examiner* — Taofiq A Solola
(74) *Attorney, Agent, or Firm* — Holtz, Holtz, Goodman & Chick, PC

(57) ABSTRACT

An object of the present invention is to provide organic solvent extracts of red algae *laurencia* sp., compounds isolated and identified therefrom, and an agent for preventing attachment of barnacles comprising them.

The present invention relates to a barnacle attachment preventive agent consisting of at least one selected from the group consisting of Laurencin, Thyrsiferol, Magireol A, Omaezallene, Hachijojimallene A and organic solvent extracts of red algae *laurencia* sp.

11 Claims, No Drawings

AGENTS FOR PREVENTING ATTACHMENT OF BARNACLE CONSISTING OF ORGANIC SOLVENT EXTRACTS OF RED ALGA *LAURENCIA* SP. AND COMPOUNDS ISOLATED THEREFROM

This application is the United States national phase application of International Application PCT/JP2008/066040 filed Sep. 5, 2008.

TECHNICAL FIELD

The present invention relates to an organic solvent extracts of red algae *laurencia* sp., compounds isolated and identified therefrom, and an agent for preventing attachment of barnacles comprising them.

BACKGROUND ART

Marine sessile organisms such as barnacles and mussels are causing serious financial damage by attaching to ships and vessels and lowering their sailing abilities, attaching to fishing nets and damaging them, and attaching to water supply and drain pipes of electric power plants and lowering their cooling efficiency. Conventionally, organotin compounds have widely been used as chemicals for preventing marine organisms from attaching to fishing nets and ship bottoms. Use of organotin compounds, however, is being regulated because of their strong toxicity and effect as environmental hormone. Since many of alternative compounds also contain copper or zinc, there is a concern about their adverse effects on the environment, and thus there is a demand for development of safe chemicals with less toxicity.

Regarding organic solvent extracts of red algae *laurencia* sp., it has been reported that laurinterol and isolaurinterol obtained from *Laurencia okamurae* possess a barnacle attachment inhibitory activity (Non-Patent Document 1).

It has also been reported that elatol and deschloroelatol obtained from *Laurencia rigida* have a barnacle attachment inhibitory activity (Non-Patent Document 2).

There is also a report that an organic solvent extract of *Laurencia obtusa* inhibited attachment of sessile organisms including barnacles in field tests (Non-Patent Document 3).

It has not been known so far, however, that organic solvent extracts of *Laurencia* sp. from Omaezaki, *Laurencia* sp. from Hachijojima, *Laurencia nipponica*, and *Laurencia thyrsifera* have a barnacle attachment inhibitory activity.

Furthermore, compound Laurencin has been known to be isolated from *Laurencia nipponica* (Non-Patent Document 4), and the total synthesis of it has also been reported (Non-Patent Document 5). Its biological activities, however, have not been reported so far.

Furthermore, compound Thyrsiferol isolated from *Laurencia thyrsifera* was also reported (Non-Patent Document 6). The compound was also isolated from *Laurencia obtusa*, and is known to have cytotoxicity (Non-Patent Document 7). It has not been known so far, however, whether it has an attachment inhibitory activity against cypris larvae of barnacles.

Furthermore, while it has been reported that compound Magireol A was isolated from *Laurencia obtusa* (Non-Patent Document 8), its biological activities have not been known so far.

In addition, *Laurencia* sp. from Omaezaki and *Laurencia* sp. from Hachijojima, are *Laurencia* sp. that have not been identified so far. Compound Omaezallene isolated from *Laurencia* sp. from Omaezaki and compound Hachijojimallene A isolated from *Laurencia* sp. from Hachijojima are compounds that have not been known so far, either.

[Non-Patent Document 1] Ryu, Geonseek; Yoon, Oh Sub. Studies on marine natural antifoulant laurinterol. Han'guk Hwankyong Uisaeng Hakhoechi (2003), 29(3), 1-8.

[Non-Patent Document 2] R. de Nys, T. Leya, R. Maximilien, A. Afsar, P. S. R. Nair, and P. D. Steinberg, The need for standardised broad scale bioassay testing: A case study using the red alga *Laurencia rigida*, Biofouling, 10(1-3) 213-224 (1996).

[Non-Patent Document 3] Da Gama B A P, Pereira R C, Carvalho A G V, et al, The effects of seaweed secondary metabolites on biofouling. Biofouling 18(1)13-20 (2002)

[Non-Patent Document 4] Irie, T., Suzuki, M. 1965. Laurencin, a constituent from *Laurencia species*; Tetrahedron Lett. 1965: (No. 16) 1091-1099.

[Non-Patent Document 5] Fujiwara, Kenshu; Yoshimoto, Saori; Takizawa, Ayumi; Souma, Shin-ichiro; Mishima, Hirofumi; Murai, Akio; Kawai, Hidetoshi; Suzuki, Takanori. Synthesis of (+)-laurencin via ring expansion of a C-glycoside derivative. Tetrahedron Letters (2005), 46(40), 6819-6822.

[Non-Patent Document 6] Blunt, J. W.; Hartshorn, M. P.; McLennan, T. J.; Munro, M. H. G.; Robinson, Ward T.; Yorke, S. C. Thyrsiferol: a squalene-derived metabolite of *Laurencia thyrsifera*. Tetrahedron Letters (1978), (1), 69-72.

[Non-Patent Document 7] Suzuki, Teruaki; Suzuki, Minoru; Furusaki, Akio; Matsumoto, Takeshi; Kato, Arata; Imanaka, Yoshihiko; Kurosawa, Etsuro. Constituents of marine plants. 62. Teurilene and thyrsiferyl 23-acetate, meso and remarkably cytotoxic compounds from the marine red alga *Laurencia obtusa* (Hudson) Lamouroux. Tetrahedron Letters (1985), 26(10), 1329-32.

[Non-Patent Document 8] Teruaki Suzuki, Satoshi Takeda, Minoru Suzuki, Etsuro Kurosawa, Arata Kato, and Yoshihiko Imanaka, Cytotoxic squalene-derived polyethers from the marine red alga *Laurencia obtuse* (Hudson) Lamouroux. Chemistry Letters (1987) pp. 361-364.

DISCLOSURE OF THE INVENTION

Problem to be Solved by the Invention

An object of the present invention is to provide organic solvent extracts of red algae *laurencia* sp., compounds isolated therefrom, and an agent for preventing attachment of barnacles comprising them.

Means for Solving the Problem

The present inventors have found as a result of an extensive effort that organic solvent extracts of red algae *laurencia* sp. and compounds isolated therefrom have an barnacle attachment preventing effect, and have completed the present invention. Therefore, (1) the present invention relates to a barnacle attachment preventive agent consisting of at least one organic solvent extract selected from the group consisting of *Laurencia* sp. from Omaezaki, *Laurencia* sp. from Hachijojima, *Laurencia nipponica*, and *Laurencia thyrsifera*;

(2) the present invention relates to Omaezallene represented by the formula:

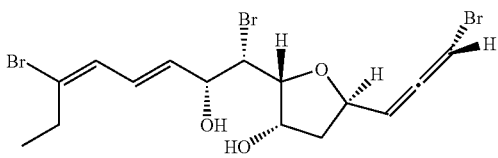

wherein =•= represents =C=;
(3) the present invention relates to Hachijojimallene A represented by the formula:

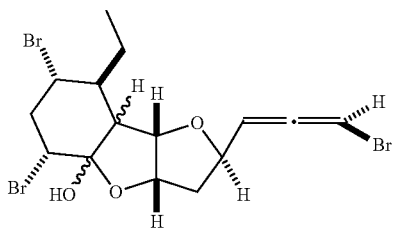

wherein =•= represents =C=;
(4) the present invention relates to a composition comprising Omaezallene and/or Hachijojimallene A;
(5) the present invention relates to a barnacle attachment preventive agent consisting of at least one selected from the group consisting of Laurencin, Thyrsiferol, Magireol A, Omaezallene and Hachijojimallene A;
(6) the present invention relates to a composition comprising the attachment preventive agent described in 1 or 5 above; and
(7) the present invention relates to a method for preventing a barnacle from attaching to a subject, comprising coating the attachment preventive agent described in 1 or 5 above to the subject, or incorporating the agent into the subject, or painting or preparing the subject with the composition described in 6 above.

Effect of the Invention

The organic solvent extracts of red algae *laurencia* sp. according to the invention and compounds isolated and identified therefrom can be used as a barnacle attachment preventive agent.

BEST MODE FOR CARRYING OUT THE INVENTION

As mentioned above, the present invention relates to a barnacle attachment preventive agent comprising organic solvent extracts of red algae *laurencia* sp. and compounds isolated and identified therefrom.

Barnacles as used in the invention mean organisms belonging to Cirripedia and Thoracica, and not limited as long as they belong to Pedunculata or Sessilia, and examples include *Amphibalanus amphitrite, Amphibalanus ebruneus, Amphibalanus reticulates, Fistrulobalanus kondakovi, Megabalanus rosa, Megabalanus volcano*, and *Balanus albicostatus*, and preferably *Amphibalanus amphitrite*.

The life cycle of barnacles is as follows: a nauplius larva hatched from a fertilized egg repeats molting for five times, and metamorphoses at the 6th molting into a cypris larva. This cypris larva attaches to a substrate and again metamorphoses at another molting into a barnacle immature, which leads a sessile life while attaching to the substrate, and thereafter repeats molting before finally turning into an adult barnacle.

The extracts and compounds according to the present invention have an action of inhibiting this attachment of cypris larvae to a substrate. Therefore, the barnacle attachment preventive agent of the present invention means an agent for preventing attachment of barnacle cypris larvae.

The attachment of a cypris larva in the present invention indicates that a cypris larva sticks to a substrate by releasing a sticking substance, and then it molts and metamorphoses into a barnacle immature, terminating its life as a plankton. Therefore, the attachment of a cypris larva is determined whether the cypris larva has been turned into a barnacle immature and is sticking to a substrate.

The red algae *laurencia* sp. of the present invention includes *Laurencia* sp. from Omaezaki, *Laurencia* sp. from Hachijojima, *Laurencia nipponica*, and *Laurencia thyrsifera*. The red algae *laurencia* sp. as used in the present invention particularly indicates *Laurencia* sp. from Omaezaki, *Laurencia* sp. from Hachijojima, *Laurencia nipponica*, and *Laurencia thyrsifera*. Inter alia, preferred are *Laurencia nipponica* and *Laurencia thyrsifera*, and more preferred is *Laurencia nipponica*.

*Laurencia* sp. from Omaezaki refers to *Laurencia* sp. collected from Omaezaki, Shizuoka-ken, Japan, which has not been identified so far. Furthermore, *Laurencia* sp. from Hachijojima refers to *Laurencia* sp. collected from Hachijojima, Tokyo, Japan, which has not been identified so far, either.

Since *Laurencia* sp. from Omaezaki and *Laurencia* sp. from Hachijojima are *Laurencia* sp. which have not been morphologically identified so far, they can be identified as *Laurencia* sp. comprising Omaezallene and Hachijojimallene A, respectively.

For organic solvent extracts of red algae *laurencia* sp. of the present invention, collected red algae *laurencia* sp. from which water has been drained off or collected red algae *laurencia* sp. which has been dried, or those made into a powder can be used. Such red algae *laurencia* sp. is extracted by immersing it in an organic solvent. The extraction temperature is, while not particularly limited, 15 to 25° C., preferably room temperature (about 20° C.), and extraction time is, while not particularly limited, one hour to one week, preferably 24 hours. The extraction operation, while not particularly limited, may or may not include stirring, and the number of extraction may be one, but much more extract can be obtained by two or more extractions. Concentrating of the organic solvent extract, while not particularly limited, can be carried out under reduced pressure, setting the temperature of hot water bath preferably at 20 to 25° C. Furthermore, this organic solvent extract may be a lipid-soluble (ethyl acetate or diethyl ether) fraction obtained by distributing residues after vacuum concentration, for example in ethyl acetate/water or diethyl ether/water. The organic solvent extract of red algae *laurencia* sp. according to the present invention may be in the form containing an organic solvent, or in the form of a residue after the removal of organic solvent.

The organic solvent includes, while not particularly limited, for example, methanol, ethyl acetate, ethanol, acetonitrile, acetone, chloroform, dichloromethane, chloroform, and a liquid mixture thereof. Preferred are methanol, ethyl acetate, chloroform and a mixture liquid thereof, and more preferred is methanol.

The preferable amount of the organic solvent extract of *Laurencia* sp. from Omaezaki for a barnacle attachment preventive agent is 10 μg/cm$^2$ or more, more preferably 100

µg/cm² or more, and even more preferably 1000 µg/cm² or more, based on the weight of the dry alga body used for the organic solvent extraction.

The preferable amount of organic solvent extract of *Laurencia* sp. from Hachijojima for a barnacle attachment preventive agent is 10 µg/cm² or more, more preferably 100 µg/cm² or more, and even more preferably 1000 µg/cm² or more, based on the weight of the dry alga body used for the organic solvent extraction.

The preferable amount of organic solvent extract of *Laurencia nipponica* for a barnacle attachment preventive agent is 10 µg/cm² or more, more preferably 100 µg/cm² or more, and even more preferably 1000 µg/cm² or more, based on the weight of the dry alga body used for the organic solvent extraction.

The preferable amount of organic solvent extract of *Laurencia thyrsifera* for a barnacle attachment preventive agent is 10 µg/cm² or more, more preferably 100 µg/cm² or more, and even more preferably 1000 µg/cm² or more, based on the weight of the dry alga body used for the organic solvent extraction.

The present invention provides Omaezallene represented by the following formula:

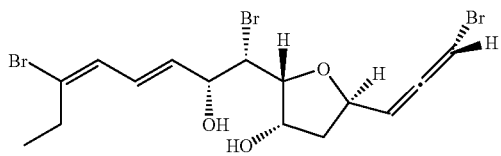

wherein =•= represents =C=.

While Omaezallene can be extracted from red algae belonging to the genus *Laurencia*, preferably *Laurencia* sp. by the method described in Examples, the organisms for extraction is not particularly limited as long as they contain Omaezallene. Furthermore, Omaezallene may be chemically synthesized or commercially obtained.

Omaezallene may be used as a barnacle attachment preventive agent. The preferable amount of Omaezallene for a barnacle attachment preventive agent is 1 µg/cm² or more, more preferably 10 µg/cm² or more, and even more preferably 100 µg/cm² or more.

The present invention provides Hachijojimallene A represented by the following formula:

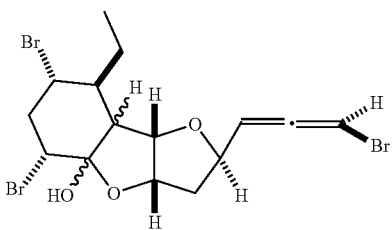

wherein =•= represents =C=.

While Hachijojimallene A can be extracted from red algae belonging to the genus *Laurencia*, preferably *Laurencia* sp. by the method described in Examples, the organisms for extraction are not particularly limited as long as they contain Hachijojimallene A. Furthermore, Hachijojimallene A may be chemically synthesized or commercially obtained.

Hachijojimallene A may be used as a barnacle attachment preventive agent. The preferable amount of Hachijojimallene A for a barnacle attachment preventive agent is 1 µg/cm² or more, more preferably 10 µg/cm² or more, and even more preferably 100 µg/cm² or more.

Laurencin used in the present invention has the following structural formula:

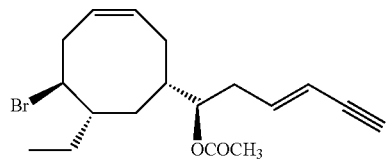

and while Laurencin can be extracted using, for example, the conventionally known method (Non-Patent Document 4) from red algae belonging to the genus *Laurencia*, preferably from *Laurencia nipponica*, the organisms for extraction are not particularly limited as long as they contain Laurencin. Furthermore, Laurencin may be chemically synthesized (Non-Patent Document 5) or commercially obtained.

The preferable amount of Laurencin for a barnacle attachment preventive agent is 1 µg/cm² or more, more preferably 10 µg/cm² or more, and even more preferably 100 µg/cm² or more.

Thyrsiferol used in the present invention has the following structural formula:

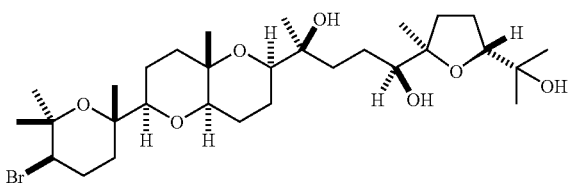

and while Thyrsiferol can be extracted using, for example, the conventionally known method (Non-Patent Documents 6, 7) from red algae belonging to the genus *Laurencia*, preferably from *Laurencia thyrsifera* and *Laurencia obutusa*, the organisms for extraction are not particularly limited as long as they contain Thyrsiferol. Furthermore, Thyrsiferol may be chemically synthesized or commercially obtained.

The preferable amount of Thyrsiferol for a barnacle attachment preventive agent is 1 µg/cm² or more, more preferably 10 µg/cm² or more, and even more preferably 100 µg/cm² or more.

The compound Magireol A used in the present invention has the following structural formula:

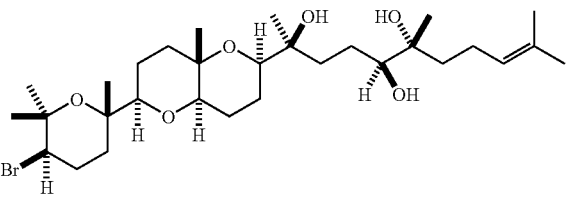

and while the compound Magireol A can be extracted using, for example, the conventionally known method (Non-Patent Document 8) from red algae belonging to the genus *Laurencia*, preferably *Laurencia obutusa*, the organisms for extraction are not particularly limited as long as they contain Magireol A. Furthermore, Magireol A may be chemically synthesized or commercially obtained.

The preferable amount of Magireol A for a barnacle attachment preventive agent is 1 μg/cm² or more, more preferably 10 μg/cm² or more, and even more preferably 100 μg/cm² or more.

The organic solvent extracts of red algae *laurencia* sp., Laurencin, Thyrsiferol, Magireol A, Omaezallene or Hachijojimallene A used in the present invention may be used alone or in combination of two or more of them as a barnacle attachment preventive agent.

The attachment preventive agent against barnacles of the present invention may use the extract or the compound in the form containing an organic solvent as it is or in the form after removal of the organic solvent as it is, or, alternatively, the agent may be used by preparing it in the form of a gel such as hydrogel, a solid, and a solution (including an emulsion or a suspension). The barnacle attachment preventive agent of the present invention can therefore incorporate a thickener, a plasticizer, a colorant or the like on an as needed basis.

As the modes of the composition comprising the attachment preventive agent of the present invention, there can be mentioned a paint used for coating artificial materials present in the sea, for example, ships, in particular, portions of ships submerged in the seawater including ship bottoms, screw propellers, helms, anchors, chains; nets such as fishing nets; ropes; floats; buoys; wave-dissipating blocks; revetments; and undersea structures, a fiber to be used for nets and ropes impregnated with the attachment preventive agent of the present invention, a plastic containing the attachment preventive agent of the present invention to be used for ships; nets; ropes; floats; buoys; and undersea structures, and a cement concrete containing the attachment preventive agent of the present invention to be used for wave-dissipating blocks; revetments; and undersea structures.

For example, the organic solvent extracts of red algae *laurencia* sp., Laurencin, Thyrsiferol, Magireol A, Omaezallene or Hachijojimallene A of the present invention is incorporated in a ratio of 0.1 to 50%, preferably 0.1 to 30%, and more preferably 0.1 to 10% based on the weight of the paint, fiber, plastic, or cement concrete.

The method for preventing attachment of barnacles using a composition containing the attachment preventive agent of the present invention comprises, when the composition is a paint containing the attachment preventive agent of the present invention, painting with the paint the subject from which the attachment of barnacles is intended to be prevented, for example, artificial materials present in the sea including ships, in particular, portions of ships submerged in the seawater including ship bottoms, screw propellers, helms, anchors, chains; nets such as fishing nets; ropes; floats; buoys; wave-dissipating blocks; revetments; and undersea structures, thereby preventing barnacles from attaching to the subject. Furthermore, when the composition is a fiber impregnated with the attachment preventive agent of the present invention, there can be mentioned a method comprising producing nets and ropes with the fiber, and thereby preventing the attachment of barnacles to the nets and ropes. Furthermore, when the composition is a plastic containing the attachment preventive agent of the present invention, there can be mentioned a method comprising preparing ships; nets; ropes; floats; buoys; and undersea structures using the plastic, thereby preventing the attachment of barnacles to the ships; nets; ropes; floats; buoys; and undersea structures. In addition, when the composition is a cement concrete containing the attachment preventive agent of the present invention, there can be mentioned a method comprising preparing wave-dissipating blocks, revetments, and undersea structures using the cement concrete, thereby preventing the attachment of barnacles to the wave-dissipating blocks and undersea structures.

Example 1

Barnacle Attachment•Metamorphosis Inhibition Test

Adult samples of *Amphibalanus amphitrite* collected from Lake Hamanako, Shizuoka-ken in the breeding season (May to November in Hamanakako) were subject to drying stimulus for about 12 hours (drying stimulus refers to taking out barnacles out of the breeding water and let them dry), and then they were put into a water bath, thereby allowing eggs to hatch into nauplius larvae (if the adults are not in a breeding season, they are subject to food satiation breeding for about two weeks at a water temperature of 20° C. to 25° C., and after subjecting to drying stimulus for about 12 hours, they are housed in a water bath to allow eggs to hatch into nauplius larvae). The nauplius larvae were put into 2 L beaker, bred at 25° C. for 24 hours under bright condition, and into the beaker was added *Chaetoceros gracilis* at the concentration of 200,000 cells/ml or more while changing water of the beaker every day (Ryusuke Kato and Reijiro Hirano: Fuchaku Seibutsu Fuyu-ki Yousei No Shiiku-houhou (Breeding Method of Floating Larvae of Sessile Organisms), Fuchaku-Seibutsu Kenkyu (Sessile Organism Study), 1(1), 11-19 (1979)). At 5th day of breeding, the nauplius larvae metamorphosed into cypris larvae, which were collected using light or the like and refrigerated (4° C.) for two days, and then used for attachment•metamorphosis inhibition tests.

Into a 24-well multi plate made of polystyrene (Corning, Inc.) was put an ethanol solution in which a methanol extract of red algae *laurencia* sp. of the present invention or the compound of the present invention was dissolved, and allowed to dry, followed by charging of 2 mL filtered seawater. Six individual cypris larvae of *Amphibalanus amphitrite* were put into each well and bred at 25° C. for two to five days, and the number of individuals that metamorphosed from cypris larvae into barnacle immatures while attaching to the plate surface, the number of individuals not attached thereto and still swimming as cypris larvae, and the number of dead individuals were counted under a stereoscopic microscope. The tests were conducted using four wells each for a same concentration of the compound of the present invention, and the tests were repeated three or more times. The concentration at which the number of dead individuals after 5 days accounted for 50% of the number of all the subject individuals, was represented by $LC_{50}$. Furthermore, the concentration at which the ratio of the number of attaching•metamorphosing individuals to the number of all the subject individuals after 2 days is one-half in comparison with the case not having the compounds of the present invention, was represented by $EC_{50}$. Concentrations (μg/ml) were represented by the value obtained by dividing the amount of the methanol extract of red algae *laurencia* sp. (μg) or the amount of the compound (μg) added per well by 2 mL of filtered seawater added per well.

Example 2

Isolation and Identification of Omaezallene

The dry alga body (250 g) of *Laurencia* sp. from Omaezaki collected from Omaezaki, Shizuoka-ken was extracted with methanol (3 L). The methanol extract was observed to have a barnacle attachment inhibitory activity (100% inhibition of attachment at 10 μg/mL based on the weight of dry alga body). The extract was vacuum concentrated, and distributed with ethyl acetate (1.5 L) and water (0.5 L). The ethyl acetate fraction (2.3 g) was subsequently subjected to silica gel column chromatography (130 g, Merck Kieselgel 60), and eluted with 200 mL of hexane, 300 mL of hexane/ethyl acetate (9:1), 300 mL of hexane/ethyl acetate (7:3), 300 mL of hexane/ethyl acetate (1:1), 300 mL of ethyl acetate, and 300 mL of ethyl acetate/methanol (9:1) in this order. The aforementioned barnacle attachment inhibition test was performed for each eluted fraction, and, as a result, the activity was observed in the ethyl acetate fraction. After concentrating the ethyl acetate fraction (504 mg), it was again subjected to silica gel column chromatography (silica gel 30 g), and eluted with 190 mL of hexane/ethyl acetate=1:1. The activity was observed in 30 mL that was eluted after the elution of 100 mL of the solvent. This activity fraction was concentrated to obtain 112 mg. After dissolving 20 mg of this fraction in acetonitrile, separations and activity assays were repeated using a reversed phase HPLC (JASCO Corporation PU-980, UV-970, 220 nm, 0-10 minutes, 60-75% acetonitrile, flow rate: 3 mL per minutes, room temperature: 25° C., Nomura Chemical Co., Ltd. Develosil ODS-T-5, 10×250 mm) until a single peak was obtained, to yield Omaezallene (10 mg).

The planar structure of this purified Omaezallene was determined by the analysis of one-dimensional and two-dimensional NMR spectral and mass spectral analysis. Stereochemistry of bromoallene moiety was determined by the optical rotation thereof, and the other relative stereochemistries were determined by NOE, etc.

IR $\nu_{max}$ (neat) cm$^{-1}$: 3386, 3050, 1954, 1093, 1033, 963, 796

LRFABMS: m/z 483/485/487/489 (1:3:3:1)

HRFABMS: m/z 482.8802 [calcd for $C_{15}H_{18}{}^{79}Br_3O_3$, 482.8806] (M−H)$^-$ $[<]_D{}^{21}$: −126.6 (c 0.215, CHCl$_3$)

$^1$HNMR (CDCl$_3$): $^{TM}$1.14 (11-15), 1.99 (H-5a), 2.10 (6-OH), 2.27 (H-5b), 2.60 (H-14), 2.87 (9-OH), 4.05 (H-7), 4.24 (11-8), 4.48 (H-9), 4.61 (H-6), 4.96 (H-4), 5.40 (H-3), 5.79 (H-10), 6.10 (H-1), 6.42 (H-11), 6.48 (H-12).

$^{13}$CNMR (CDCl$_3$): $^{TM}$13.6 (C15), 29.9 (C14), 40.4 (C5), 55.7 (C8), 73.1 (C9), 73.4 (C6), 74.2 (C1), 76.2 (C4), 83.9 (C7), 101.1 (C3), 127.5 (C11), 130.2 (C12), 131.5 (C10), 132.6 (C13), 201.3 (C2).

While this purified Omaezallene inhibited at a low concentration (EC$_{50}$ 0.22 μg/mL) the attachment•metamorphosis of cypris larvae of *Amphibalanus amphitrite*, the toxicity was low (LC$_{50}$ 3.4 μg/mL).

Example 3

Isolation and Identification of Hachijojimallene A

The dry alga body (62 g) of *Laurencia* sp. from Hachijojima collected from Hachijojima, Tokyo was extracted with methanol (500 mL). The methanol extract was observed to have a barnacle attachment inhibitory activity (100% inhibition of attachment at 10 μg/mL based on the weight of dry alga body). The extract was vacuum concentrated, and distributed with ethyl acetate (300 mL) and water (100 mL). The ethyl acetate fraction (700 mg) was subsequently subjected to silica gel column chromatography (Merck Kieselgel 60, 100 g), and eluted with 300 mL of hexane, 300 mL of hexane/ethyl acetate (9:1), 150 mL of hexane/ethyl acetate (7:3), 300 mL of hexane/ethyl acetate (1:1), 300 mL of ethyl acetate, and 300 mL of ethyl acetate/methanol (9:1) in this order. The attachment inhibitory activity was observed in the fraction eluted with the third hexane/ethyl acetate=7:3. This hexane/ethyl acetate=7:3 fraction (220 mg) was again subjected to silica gel column chromatography, and eluted with hexane/ethyl acetate=3:1, from which 20, 10, 10, 10, 10, 10, 10, and 30 mL were aliquoted. The fifth fraction (40.2 mg) and the sixth fraction (34.7 mg) which were observed to have the attachment inhibitory activity were each subjected to PTLC (Preparative Thin Layer Chromatography, Merck Kieselgel 60, 20×20 cm) and eluted with hexane/ethyl acetate=3:1. The portions each having a Rf value of 0.3 were put together (the fifth 12.4 mg+the sixth 11.8 mg), and again subjected to PTLC, and separations and activity assays were repeated with hexane/ethyl acetate=1:1 until its purity was verified by a one-dimensional NMR, to yield Hachijojimallene A (7.0 mg).

The planar structure of this purified Hachijojimallene A was determined by the analysis of one-dimensional and two-dimensional NMR spectral and mass spectral analysis. Stereochemistry of bromoallene moiety was determined by the optical rotation thereof, and the other relative stereochemistries were determined by NOE, etc.

IR $\nu_{max}$ (neat) cm$^1$: 3490, 3050, 1957, 1258, 1165, 1039, 959, 863, 800, 756

HRAPCIMS: m/z 466.8851 [calcd for $C_{15}H_{18}{}^{79}Br_3O_2$, 466.8851] (M+H−H$_2$O)$^+$, m/z 386.9590 [calcd for $C_{15}H_{17}{}^{79}Br_2O_2$, 386.9590] (M−Br−H$_2$O)$^+$ $[<]_D{}^{24}$: −88.2 (c 0.13, CHCl$_3$)

$^1$HNMR (CDCl$_3$): $^{TM}$1.03 (11-15), 1.47 (H-14b), 1.81 (H-5b), 1.97 (H-13), 2.11 (11-14a), 2.26 (H-5a), 2.50 (H-11b), 2.75 (H-11a), 2.76 (H-8), 3.79 (H-12), 4.07 (H-10), 4.56 (11-6), 4.60 (H-7), 4.73 (H-4), 5.45 (H-3), 6.08 (H-1).

$^{13}$CNMR (CDCl$_3$): $^{TM}$11.5 (C15), 24.7 (C14), 39.3 (C5), 44.3 (C11), 44.7 (C13), 50.5 (C8), 51.3 (C12), 53.6 (C10), 73.8 (C4), 74.1 (C1), 79.4 (C6), 81.7 (C7), 99.4 (C3), 102.1 (C9), 201.9 (C2).

While this purified Hachijojimallene A inhibited at a low concentration (EC$_{50}$ 0.15 μg/mL) the attachment•metamorphosis of cypris larvae of *Amphibalanus amphitrite*, the toxicity was low (LC$_{50}$ 9.8 μg/mL).

Example 4

Isolation and Identification of Laurencin

The red algae *Laurencia nipponica* (50 g, semidry weight) collected from Oshoro-wan, Otaru-shi, Hokkaido was immersed in methanol (1,000 mL) for five days and extracted therewith. The methanol extract was observed to have a barnacle attachment inhibitory activity (100% inhibition of attachment at 10 μg/mL based on the weight of dry alga body). The extraction liquid was vacuum concentrated using an evaporator, and then it was distributed with diethyl ether (300 mL) and water (150 mL). The diethyl ether layer was dehydrated with anhydrous sodium sulfate, and vacuum concentrated after filtration treatment. The obtained lipid-soluble fraction (1.3 g) was subjected to silica gel column chromatography (100 g, Merck Kieselgel 60, 70-230 mesh), and eluted with 200 mL of hexane, 200 mL of hexane/ethyl acetate (9:1), 200 mL of hexane/ethyl acetate (3:1), 200 mL of hexane/ethyl acetate (1:1), and 200 mL of ethyl acetate in this order. The solvent of the fraction eluted with hexane/ethyl acetate (3:1) was removed and the obtained crystalline substance was recrystallized from a hot methanol to yield 75 mg of pure laurencin. Various spectrum data of the isolated compound consisted with those of Non-Patent Document 5.

This purified Laurencin inhibited at a low concentration ($EC_{50}$ 0.23 μg/mL) the attachment•metamorphosis of cypris larvae of *Amphibalanus amphitrite*. Furthermore, it showed no toxicity at all to larvae even at 100 μg/mL.

Example 5

Isolation and Identification of Thyrsiferol

Red algae *Laurencia obtusa* (43 g, dry weight) collected from Oshoro-wan, Otaru-shi, Hokkaido was immersed in methanol (1,000 mL) for three days and extracted therewith. The methanol extract was observed to have a barnacle attachment inhibitory activity (100% inhibition of attachment at 10 μg/mL based on the weight of dry alga body). The extraction liquid was vacuum concentrated using an evaporator, and then distributed with diethyl ether (300 mL) and water (150 mL). The diethyl ether layer was dehydrated with anhydrous sodium sulfate and vacuum concentrated after filtration treatment. The obtained lipid-soluble fraction was subjected to silica gel column chromatography (100 g, Merck Kieselgel 60, 70-230 mesh) and eluted with 200 mL of hexane, 200 mL of hexane/ethyl acetate (9:1), 200 mL of hexane/ethyl acetate (3:1), 200 mL of hexane/ethyl acetate (1:1), and 200 mL of ethyl acetate in this order. The fraction eluted with ethyl acetate was separated with a preparative thin layer chromatography (Merck Kieselgel $60F_{254S}$, solvent; hexane/ethyl acetate (1:1)) and high-performance liquid chromatography (JASCO Corporation, Column: Finepak SIL C18, detected with UV: 215 nm, solvent: water/methanol (5:95)) to yield 4.0 mg of Thyrsiferol. Various spectrum data of the isolated compound consisted with those of Non-Patent Documents 7 and 8.

This purified Thyrsiferol inhibited at a low concentration ($EC_{50}$ 0.11 μg/mL) the attachment•metamorphosis of cypris larvae of *Amphibalanus amphitrite*. Furthermore, the toxicity to larvae was low ($LC_{50}$ 2.5 μg/mL).

Example 6

Isolation and Identification of Magireol A

Red algae *Laurencia obtusa* (43 g, dry weight) collected from Oshoro-wan, Otaru-shi, Hokkaido was immersed in methanol (1,000 mL) for three days and extracted therewith. The methanol extract was observed to have a barnacle attachment inhibitory activity (100% inhibition of attachment at 10 μg/mL based on the weight of dry alga body). The extraction liquid was vacuum concentrated using an evaporator, and then distributed with diethyl ether (300 mL) and water (150 mL). The diethyl ether layer was dehydrated with anhydrous sodium sulfate, and vacuum concentrated after filtration treatment. The obtained lipid-soluble fraction (1.01 g) was subjected to silica gel column chromatography (100 g, Merck Kieselgel 60, 70-230 mesh) and eluted with 200 mL of hexane, 200 mL of hexane/ethyl acetate (9:1), 200 mL of hexane/ethyl acetate (3:1), 200 mL of hexane/ethyl acetate (1:1), and 200 mL of ethyl acetate in this order. The fraction eluted with hexane/ethyl acetate (1:1) was separated with a preparative thin layer chromatography (Merck Kieselgel $60F_{254S}$, solvent; hexane/ethyl acetate (1:1)) and high-performance liquid chromatography (JASCO Corporation, Column: Finepak SIL C18, detected with UV: 215 nm, solvent: water/methanol (5:95)) to yield 2.5 mg of Magireol A. Various spectrum data of the isolated compound consisted with those of Non-Patent Document 9.

This purified Magireol A inhibited at a low concentration ($EC_{50}$ 0.30 μg/mL) the attachment•metamorphosis of cypris larvae of *Amphibalanus amphitrite*. Furthermore, the toxicity to larvae was low ($LC_{50}$ 14.4 μg/mL).

INDUSTRIAL APPLICABILITY

According to the present invention, it is possible to provide paints, fibers, plastics, cement concretes highly safe to fishes and shellfishes and human body for preventing attachment of barnacles to artificial materials that are present in the sea, for example, ships, in particular portions of ships submerged in the seawater including ship bottoms, screw propellers, helms, anchors, chains; nets such as fishing nets; ropes; floats; buoys; wave-dissipating blocks; revetments; and undersea structures.

The invention claimed is:

1. A barnacle attachment preventive agent consisting of at least one organic solvent extract selected from the group consisting of *Laurencia* sp. from Omaezaki, *Laurencia* sp. from Hachijojima, and *Laurencia thyrsifera*.

2. Omaezallene represented by the formula:

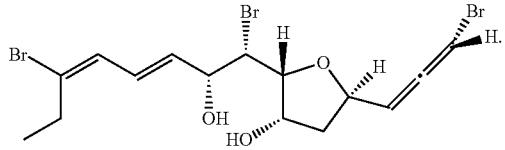

3. Hachijojimallene A represented by the formula:

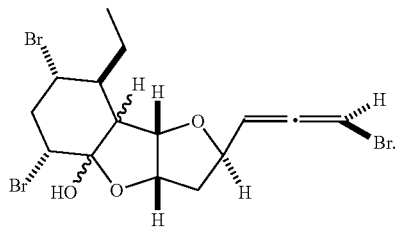

4. A composition comprising Omaezallene and/or Hachijojimallene A.

5. A barnacle attachment preventive agent consisting of at least one selected from the group consisting of Laurencin, Thyrsiferol, Magireol A, Omaezallene and Hachijojimallene A.

6. A composition comprising the attachment preventive agent according to claim 1 and a thickener, a plasticizer or a colorant.

7. A method for preventing a barnacle from attaching to a subject, comprising coating the subject with the attachment preventive agent according to claim 1.

8. A composition comprising the attachment preventive agent according to claim 5 and a thickener, a plasticizer or a colorant.

9. A method for preventing a barnacle from attaching to a subject, comprising coating the subject with the attachment preventive agent according to claim 5.

10. A method for preventing a barnacle from attaching to a subject, comprising incorporating the attachment preventive agent according to claim 1 into the subject.

11. A method for preventing a barnacle from attaching to a subject, comprising incorporating the attachment preventive agent according to claim 5 into the subject.

* * * * *